United States Patent [19]

Demarcq et al.

[11] 4,034,022
[45] July 5, 1977

[54] PHOSPHORIC ESTERS OF POLYFLUORINATED ALCOHOLS, AND THEIR PREPARATION

[75] Inventors: Michel Demarcq; Joseph Sleziona, both of Lyon, France

[73] Assignee: Produits Chimiques Ugine Kuhlmann, Paris, France

[22] Filed: Dec. 9, 1971

[21] Appl. No.: 206,512

[30] Foreign Application Priority Data

Dec. 9, 1970 France ............................ 70.44290

[52] U.S. Cl. ............................ 260/955; 260/246 B; 260/950; 260/972; 260/977

[51] Int. Cl.$^2$ ...................... C07F 9/09; C07F 9/12; C07F 9/14; C07F 9/24

[58] Field of Search ........... 260/955, 972, 977, 950

[56] References Cited

UNITED STATES PATENTS 3,100,220  8/1963  Smith .......................... 260/977

Primary Examiner—Richard L. Raymond
Attorney, Agent, or Firm—Pennie & Edmonds

[57] ABSTRACT

Phosphoric esters of polyfluorinated alcohols are disclosed comprising at least one isomer of phosphorous esters of polyfluorinated alcohols, or one of the derivatives thereof, said esters and derivatives thereof corresponding to the general formula:

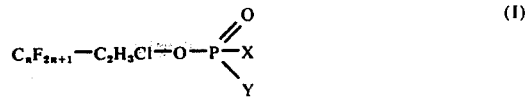

said two isomers corresponding to formulae (II) and (III):

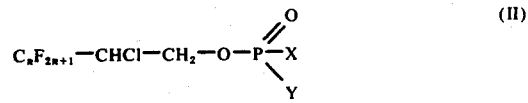

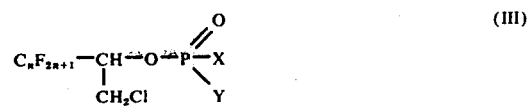

wherein $C_nF_{2n+1}$ is a perfluorinated aliphatic chain, $n$ is an integer from 2 to 18, X and Y are the same or different and are each a halogen atom, a hydroxy radical, the group OM in which M is a metallic equivalent, or an alkoxy, chloroalkoxy, hydroxypolyalkylenoxy, aryloxy, or —NZZ' group in which Z and Z' are the same or different and are each a hydrogen atom or an alkyl, cycloalkyl or aryl group.

The preparation of phosphoric esters having the general formula (I) and mixtures of the isomers (II) and (III) thereof are also disclosed.

9 Claims, No Drawings

PHOSPHORIC ESTERS OF POLYFLUORINATED ALCOHOLS, AND THEIR PREPARATION

BACKGROUND OF THE INVENTION

1. Field of the Invention

This invention relates to phosphoric esters of polyfluorinated alcohols, the derivatives thereof and their preparation.

2. Description of the Prior Art

Polyfluorinated phosphorus chain compounds are in great demand. Those which are polar enough, particularly those which are terminated by the acid group $PO_3H_2$, eventually neutralized, are appreciated for their surface properties and for the hydrophobic and oleophobic properties they impart to textiles, plastics, leather, waxes and the like. They are used as emulsifying agents in emulsion polymerization of fluorinated olefins (U.S. Pat. Nos. 2,559,754 and 2,676,985), as leveling and anti-stain agents for wax-polishes and emulsion brightening agents (U.S. Pat. No. 3,083,224 and French Pat. No. 1,454,535), or as additives for chromium plating baths (U.S. Pat. No. 3,194,840). Known compounds of this family are illustrated by phosphonic acids of formula $C_nF_{2n+1}(-CH_2)_m-PO_3H_2$ (French Pat. No. 1,454,535) or formula $H-C_nF_{2n}-PO_3H_2$ (U.S. Pat. No. 2,559,754), and by partial phosphoric esters of the formula $[C_nF_{2n+1}(CH_2)_mO]_pPO\ (OH)_{3-p}$ (U.S. Pat. No. 3,083,224), at least one of these compounds being sold under the name of ZONYL S 13, the latter being a trademark of Du Pont de Nemours.

Other phosphorus compounds having a polyfluorinated chain are used as lubricating agents or additives therefore; for example, neutral phosphoric esters having the formula $(C_nF_{2n+1}-CH_2O)_3PO$ (U.S. Pat. No. 2,888,481), esters of polyfluorinated phosphonic acids such as $H(CF_2)_n(CH_2)_3-PO(OCH_3)_2$ (French Pat. No. 1,454,535) and esters of polyfluorinated alcohols of benzene phosphonic acid (U.S. Pat. No. 3,337,665).

Similar compounds are used as hydraulic fluids: for example, phosphoric esters of polyfluorinated alcohols (U.S. Pat. Nos. 2,754,317 and 2,754,318), phosphonic esters of polyfluorinated alcohols (U.S. Pat. No. 3,246,030) or of polyfluoroalkylphenols (French Pat. No. 1,430,849), phosphoramidates of polyfluorinated alcohols (French Pat. No. 1,450,918) or esters of N - polyfluoroalkyl phosphoramidic acids (Belgian Pat. No. 672,659).

SUMMARY OF THE INVENTION

This invention relates to phosphoric esters of polyfluorinated alcohols comprising at least one isomer of phosphoric esters of polyfluorinated alcohols, or one of the derivatives thereof, said esters and derivatives thereof corresponding to the general formula:

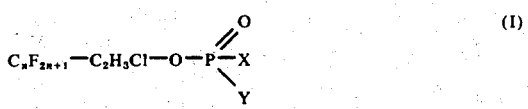

said two isomers corresponding to formulae (II) and (III):

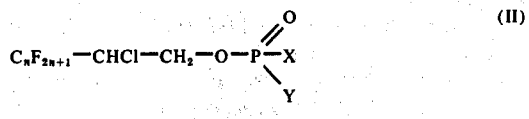

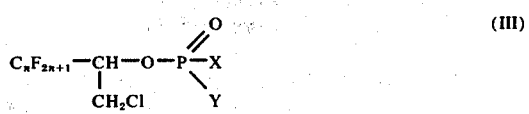

wherein $C_nF_{2n+1}$ is a perfluorinated aliphatic chain, $n$ is an integer from 2 to 18, X and Y are the same or different and are each a halogen atom, a hydroxyl radical, the group OM in which M is a metallic equivalent or an alkoxy, chloroalkoxy, hydroxypolyalkyleneoxy, aryloxy or $-NZZ'$ group in which Z and $Z'$ are the same or different and are each a hydrogen atom or an alkyl, cycloalkyl or aryl group.

The compounds of this invention can be prepared by oxidizing phosphorylation or oxidizing phosphonylation of olefins as hereinafter explained.

One of the chief advantages of the phosphoric esters of this invention is that they can be readily obtained from commonly available raw materials, such as phosphorus chlorides and olefins of the formula $C_nF_{2n+1}-CH=CH_2$. Phosphorus chlorides are indeed very inexpensive commercial products and the olefins are readily prepared by dehydroiodination of 2-perfluoroalkyl ethyl iodides of the formula $C_nF_{2n+1}-CH_2-CH_2I$, or are obtained in a more economical manner as fatal by-products of some synthesis processes involving such iodides.

Another advantage of the compounds of this invention is that the ester bonding phosphorus to the polyfluorinated group is very stable to acid hydrolysis and to oxidants, this property being often requested for products of this type, especially when they are intended to be used in acid baths for metal treatment (pickling, brightening, chromium plating, passination and the like).

DESCRIPTION OF THE PREFERRED EMBODIMENTS

To prepare the esters and derivatives thereof corresponding to formula (I), mixtures of at least one of the isomers corresponding to formulae (II) and (III), it is convenient to begin with the preparation of chlorophosphates of the formula:

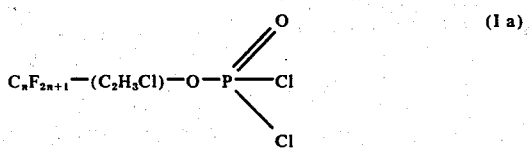

which are mixtures of at least one of the isomers

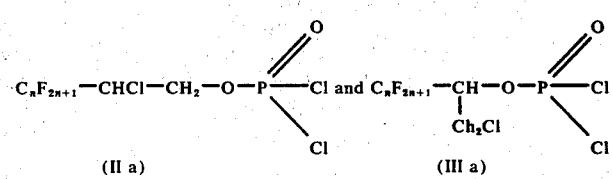

the above structures having been confirmed by chemical analysis, mass spectrometry and proton nuclear magnetic resonance.

Thereafter the esters and the other derivatives are prepared by substitution of appropriate groups for chlorine atoms.

The following process is preferred for the preparation of chlorophosphates.

According to this process, an oxygen containing gas is contracted with, simultaneously, phosphorus trichloride and an olefin having the formula $C_nF_{2n+1}-CH=CH_2$.

The general reaction can be represented as follows:

$$C_nF_{2n+1}-CH=CH_2+xPCl_3+\frac{x+1}{2}O_2\longrightarrow \quad (1)$$

$$z\,(IIa)+(1-z)\,(IIIa)+(x-1)\,POCl_3$$

This result is surprising because the reaction of oxygen on phosphorus trichloride in the presence of an olefin was known to lead to phosphonates and not to phosphates, according to reactions (2) (addition to the double bond) and (3) (statistic substitution along saturated chains R and $R^1$)

$$R-CH=CHR^1+xPCl_3+(x/2)O_2\rightarrow z \quad (2)$$
$$(R-CHCl-CHR^1-POCl_2)+(1-z)(R^1-CH-CHR-POCl_2)+(x-1)POCl_3$$

$$R-CH=CHR^2-CH_2R^3+xPCl_3+(x/2)O_2\rightarrow \quad (3)$$
$$R-CH=CHR^2-CHR^3-POCl_2+(x-1)POCl_3+HCl$$

Reaction (1) will be hereinafter referred to as "oxidizing phosphorylation" in contrast to reactions (2) and (3) which are commonly referred to as "oxidizing phosphonylation of olefins." For full information on this latter type of reaction, the following references can, for example, be consulted: original publications of Zinoviev, Soborovski et al. (Doklad. Akad. Navk. SSSR 1949, 67, p. 293; J. Obsch. Khim 1958, 28, p. 317; ibid 1959, 29, p. 615, 1139, 3556, 3947, 3954) and original publications of Rochlitz and Vilcsek (Angew. Chem. 1962, 74, p. 24,970; German Pat. No. 1,103,922).

The exothermic reaction (1) is advantageously carried out at a temperature between −20° and +120° C, the preferred range being +20° to +60° C. The oxygen containing gas may be pure oxygen, air or oxygen blended with an inert gas such a nitrogen, carbon dioxide or argon. The operating pressure is preferably atmospheric pressure, though it is possible to operate at reduced pressure or at a pressure up to about 400 psi.

In a preferred embodiment, the carefully dried oxygen containing gas is bubbled into a liquid mixture composed of phosphorus trichloride and the fluorinated olefin by means of an appropriate diffusing device, for example, a sintered glass plate, the reactor being cooled so that the temperature is maintained in the above specified range. The gas which issues from the reactor vent can be passed through a pump and after eventual addition of oxygen, reinjected into the reactor.

It is to be noted that these gases generally contain only minor quantities of hydrochloric acid thus showing that oxidizing phosphorylation (1) is not accompanied by a substitution reaction like (3) and that the chlorophosphates IIa and IIIa do not spontaneously dechlorohydrate according to reactions (4) or (5):

(4) $\quad C_nF_{2n+1}-CHCl-CH_2-O-POCl_2\longrightarrow$
$\quad\quad C_nF_{2n+1}-CH=CH-O-POCl_2+HCl$ (5)
$$C_nF_{2n+1}-\underset{\underset{CH_2Cl}{|}}{CH}-O-POCl_2\longrightarrow$$
$$C_nF_{2n+1}-\underset{\underset{CH_2}{\|}}{C}-O-POCl_2+HCl$$

When the reacted fluorinated olefin is gaseous at the reaction temperature, another embodiment is to bubble a mixture composed of this olefin, oxygen and eventually an inert gas into liquid phosphorus trichloride.

The oxidizing phosphorylation (1) always leads to substantial quantities of phosphorus oxychloride; it will be thus advantageous, in order to obtain a high conversion ratio, to react phosphorus trichloride in excess. The molar ratio $PCl_3/C_nF_{2n+1}-CH=CH_2$ will be thus between, for example, 0.5 and 20, the preferred range being 1 to 5.

The chlorophosphates IIa and IIIa can be prepared by other methods. For instance a fluorinated epoxy compound

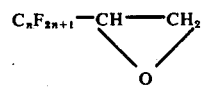

may be reacted with phosphorus oxychloride in excess in the presence of a catalyst such as titanium or zirconium tetrachloride, stannic chloride or aluminum chloride, according to reaction (6)

$$C_nF_{2n+1}-CH\underset{O}{\overset{}{\diagdown\diagup}}CH_2+POCl_3\xrightarrow{TiCl_4} IIa+IIIa \quad (6)$$

The foregoing epoxy compounds can be obtained by reaction of hydrogen peroxide with olefins having the formula $C_nF_{2n+1}-CH=CH_2$.

The chlorophosphates IIa and IIIa can also be synthesized by treating a chlorohydrin $C_nF_{2n+1}-CHOH-CH_2Cl$ or $C_nF_{2n+1}-CHCl-CH_2OH$ with an excess of phosphorus oxychloride, eventually in the presence of a tertiary amine.

The foregoing chlorohydrins or mixtures thereof can be prepared by reacting hydrochloric acid and epoxy compounds

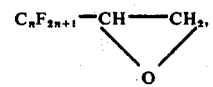

or hypochlorous acid and olefins $C_nF_{2n+1}-CH=CH_2$.

The esters and the other phosphorus fluorinated compounds according to the invention can be readily obtained from chlorophosphates IIa and IIIa in known and conventional ways.

For example, to obtain a free acid of type II or III (wherein X = Y = OH), a compound IIa or IIIa will be reacted with water, eventually in the presence of a third solvent.

To obtain alkyl or aryl ester of formulae II and III, wherein X and Y are each an alkoxy or aryloxy group, respectively, a chloride IIa or IIIa is reacted with an alcohol or a phenol, eventually in the presence of a tertiary amine, or with an alkaline metal alkoxide or phenoxide.

To obtain a N, N, N', N', tetra-alkyl phosphorodiamidate (compounds of formulae II and III wherein X and Y are each a dialkylamino radical), a chloride IIa or IIIa is treated with at least 4 molar equivalents of dialkylamine in hydrocarbon solvent, the resulting amine hydrochloride is then separated by filtration and the solvent is evaporated to recover the desired phosphorodiamidate.

Other compounds of formula II or III (X and Y being the same or different) which can be derived from corresponding chlorophosphates IIa and IIIa, can be easily imagined and synthesized by those who are skilled in the art.

The compounds according to the invention are liable to find numerous applications as wetting, emulsifying or foaming agents, particularly when a tensioactive agent resistant to acids and oxidants is needed, as leveling or anti-stain agents for polishes or emulsion paints, as corrosion inhibitors, solvent evaporation retarders or as hydrophobic and oleophobic agents.

The following non-limitative examples illustrate the compounds of the invention and the preparation thereof.

EXAMPLE 1

In a "Pyrex" glass reactor immersed in a cooling bath and provided with sintered glass diffusing means for gas, thermometer and reflux condenser, were charged 120 parts of olefin $C_8F_{17}$—CH=$CH_2$ and 148 parts of phosphorus trichloride, the molar ratio $PCl_3$/olefin being 4.0. Dry oxygen was bubbled into the reactor while maintaining a temperature between 30° and 35° C. After 3 hours and 30 minutes, there was no more exothermicity and the oxygen bubbling was stopped. The reaction released only 0.3 parts of hydrochloric acid. The phosphorus oxychloride by-product was stripped off together with the non-reacted olefin by means of a distillation under 25 mm Hg. The crude residue was then distilled under higher vacuum yielding as the main fraction 63 parts of a colorless liquid between 113° and 118° C under 1.1 to 1.4 mm Hg and having a refractive index $n_D^{1.85} = 1.3626$. Chemical analysis was as follows:

|  | P% | total Cl% | hydrolyzable Cl |
|---|---|---|---|
| found | 5.08 | 17.48 | 11.63 |
| calculated for $C_{10}H_3Cl_3F_{17}O_2P$ | 5.04 | 17.32 | 11.53 |

The term "hydrolyzable Cl" herein designates the chlorine atom bound to phosphorus which is hydrolyzable by mere ebullition with water. The mass spectrum showed 614 as principal molecular weight which exactly corresponds to isotopic formula $^{12}C_{10}$, $^1H_3$, $^{35}Cl_3$, $^{19}F_{17}$, $^{16}O_2$, $^{31}P$. The olefin yield was 38%.

EXAMPLE 2

The acid chloride obtained in Example 1 was hydrolyzed by stirring with cold water for 48 hours. Vacuum evaporation left a solid acid residue, $C_{10}H_3ClF_{17}O$—$PO_3H_2$, which was crystalline and colorless and which melted at a temperature between 125° and 128° C. The sodium hydroxide potentiometric titration curve of said acid showed two inflections corresponding to acid numbers $1A_1 = 95$ and $1A_2 = 192$ mg KOH/g (calculated values for $C_{10}H_5ClF_{17}$—$O_4P$ : $1A_1 = 97$, $1A_2 = 194$).

EXAMPLE 3

Example 1 was repeated except that olefin $C_{10}F_{21}$—CH=$CH_2$ was substituted for olefin $C_8F_{17}$—CH=$CH_2$ on the basis of one mole per mole; chlorophosphate $C_{12}H_3ClF_{21}$—O—$POCl_2$ was obtained as a tallow-like solid melting between 41° and 43° C and distilling between 134° and 138° C under 0.55 mm Hg. Chemical analysis was:

|  | P% | total Cl% | hydrolyzable Cl |
|---|---|---|---|
| found | 4.50 | 15.01 | 9.66 |
| calculated for $C_{12}H_3Cl_3F_{21}O_2P$ | 4.33 | 14.89 | 9.93 |

The olefin yield was 30%.

EXAMPLE 4

The chlorophosphate obtained in Example 3 was hydrolyzed as in example 2, yielding a crystalline, colorless solid melting at 145°–148° C. The sodium hydroxide potentiometric titration curve showed acid numbers $1A_1 = 82.4$ and $1A_2 = 166.7$ mg KOH/g (calculated values for $C_{12}H_5ClF_{21}O_4P$ : $1A_1 = 82.7$; $1A_2 = 165.4$), which corresponds to formula $C_{12}H_3ClF_{21}$—O—$PO_3H_2$.

EXAMPLE 5

Example 1 was repeated except that olefin $C_6F_{13}$—CH=$CH_2$ was substituted for olefin $C_8F_{17}$—CH=$CH_2$ on the basis of one mole per mole. A colorless oil was obtained, having a refractive index $n_D^{16.5} = 1.3700$ and distilling at a temperature between 96° and 98° C under 1.6 to 1.8 mm Hg. The formula of said oil was $C_8H_3ClF_{13}$—O—$POCl_2$. Chemical analysis was as follows:

|  | P% | total Cl% | hydrolyzable Cl |
|---|---|---|---|
| found | 6.21 | 21.07 | 13.78 |
| calculated for $C_8H_3Cl_3F_{13}O_2P$ | 6.02 | 20.67 | 13.78 |

The olefin yield was 46.8%.

EXAMPLE 6

The chlorophosphate of example 5 was hydrolyzed as in example 2. A colorless crystalline solid was obtained melting between 95° and 99° C. The sodium hydroxide potentiometric titration curve showed acid numbers $1A_1 = 121$ and $1A_2 = 246$ mg KOH/g (calculated values for $C_8H_5ClF_{13}O_4P$: $1A_1 = 118.2$; $1A_2 = 236.4$). The formula of said solid was $C_8H_3ClF_{13}$—O—$PO_3H_2$.

EXAMPLE 7

To a mixture of epoxide

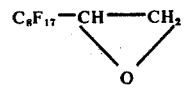

23 parts, and phosphorus oxychloride 77 parts, were added titanium tetrachloride 0.3 part. The mixture was stirred for 20 hours at 50°–60° C, then phosphorus oxychloride in excess was stripped off under vacuum and the crude chlorophosphate $C_{10}H_3ClF_{17}$—O—$POCl_2$ was hydrolzyed without distillation. Thus a solid meeting of 108°–112° C was obtained; it was the acid $C_{10}H_{13}ClF_{17}$—O—$PO_3H_2$ with small quantities of diester $(C_{10}H_{13}ClF_{17}O)_2PO_2H$ as contaminant. An equal part mixture of this acid together with the acid of the same composition obtained in example 2 melted between 108° and 122° C. The lack of a cryoscopic drop of the ending melting point suggests that in the two cases the same monoester is actually involved.

EXAMPLE 8

A mixture of chlorophosphate $C_8H_3ClF_{13}$—O—$POCl_2$ 51.5 g (0.1 mole) obtained according to example 5 and phenol 23.6 g (0.24 mole), together with 0.8 g of magnesium as a catalyst, was heated at reflux for 3 hours at 80°–110° C under a residual pressure of 25–35 mm Hg. The temperature was increased to 200° C over 30 minutes, under a pressure of 16 mm Hg, so as to strip off phenol in excess. The residue was taken up in ethyl ether and the resulting solution was washed once with 1% aqueous solution of sodium acid carbonate, then once again with diluted hydrochloric aqueous solution, and finally twice with water. After evaporation of the ether, a colorless solid was obtained, with a yield of 78%, melting point 35°–37° C, refractive index $n_D^{41}$ = 1.4315, formula $C_8H_3ClF_{13}$—O—PO $(O-C_6H_5)_2$.

EXAMPLE 9

To a solution of absolute alcohol 0.3 mole and anhydrous pyridine, 0.2 mole, in 260 ml petroleum ether, was added drop by drop, chlorophosphate $C_8H_3ClF_{13}O$—$POCl_2$ (0.1 mole) obtained according to example 5, while stirring and maintaining temperature between 25° and 35° C. The mixture was then heated at reflux for 2 hours, then filtered, and the light fractions were stripped off. The crude phosphate residue was distilled under high vacuum and there was obtained with a yield of 84%, the ester $C_8H_3ClF_{13}$—O—$PO(OC_2H_5)_2$ as a colorless liquid, refractive index $n_D^{20}$ = 1.3620, distilling between 123° and 124° C under 1.3 mm Hg, chlorine content: 6.60%, phosphorus content: 5.69% (theoretical contents respectively 6.66 and 5.82%).

EXAMPLE 10

57.8 g (0.1 mole) of the acid $C_{10}H_3ClF_{17}$—O—$PO_3H_2$ obtained according to example 2 were stirred without heating together with epichlorhydrin 59 g (0.64 mole). The mixture which was at first heterogeneous rapidly become homogeneous and at the same time, the temperatures spontaneously rose to 95° C. The reaction was completed by heating at 125° C for 30 minutes, then epichlorhydrin in excess was stripped off under vacuum. The cooled residue was as a pale yellow jelly, yielding foaming water solutions having a pH of 3 to 4. Its refractive index was $n_D^{32}$ = 1.4170. Chemical analysis gave Cl% = 17.35 and P% = 3.53, which corresponds to formula

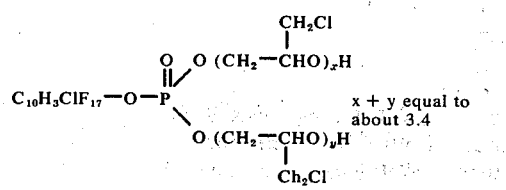

x + y equal to about 3.4

EXAMPLE 11

Example 1 was repeated with substitution of olefin $C_4F_9$—CH=$CH_2$ for olefin $C_8F_{17}$—CH=$CH_2$ on the base of one molar per mole. There was obtained chlorophosphate $C_6H_3ClF_9$—O—$POCl_2$ as a colorless liquid distilling between 103° and 104° C under 16 mm Hg and having a refractive index $n_D^{20}$ = 1.3793. The olefin yield was 47.6%. The hydrolyzable chlorine content was 17.33 (in theory: 17.10).

EXAMPLE 12

Drop by drop, 42 g chlorophosphate (0.1 mole) $C_6H_3ClF_9$—O—$POCl_2$ obtained according to example 11 where added to 39 g morpholine (0.45 mole) in 120 ml petroleum ether. The temperature spontaneously rose to 30° C and there appeared a morpholinium chloride precipitate which was left standing over 12 hours then filtered. By evaporation of the filtrate, 48 g of dimorpholide $C_6H_3ClF_9$—O—$PO[N(C_2H_4)_2O]_2$ were obtained, as a pale yellow oil, water soluble, having a refractive index $n_D^{25}$ = 1.4314, and chlorine and nitrogen contents of 6.35 and 5.43% respectively (theoretical contents 6.87 and 5.42 respectively).

EXAMPLE 13

9 g of the acid $C_{10}H_3ClF_{17}$—O—$PO_3H_2$ obtained according to example 2 were dispersed in 50 cm3 water. To the resulting gel was gradually added, while stirring, a solution of 2.20 g sodium carbonate in 50 cm3 water. The very foaming resulting solution was evaporated, to a constant weight basis, in a 600 cm3 crystallizing dish on water bath, then in an oven at 105° C. The monosodium salt $C_{10}H_3ClF_{17}$—O—$PO_3HNa$ was finally obtained as a clear cream-colored solid, yielding water solution having a pH of about 6.

EXAMPLE 14

Example 13 was repeated except that twice the quantity of sodium carbonate was employed. Disodium salt $C_{10}H_3ClF_{17}$—O—$PO_3Na_2$ was then obtained, as a clear cream-colored solid, yielding water solution having a pH of about 8.6. The following Table 1 shows some values of surface tensions (dyne/cm at 20° C) of aqueous solutions of acids $C_nF_{2n+1}$—$C_2H_3Cl$—O—$PO_3H_2$ obtained in the examples 2, 4 and 6.

TABLE I

| Concentration in $C_nF_{2+1}$—$CH_2H_3Cl$—$OPO_3H_2$ (g/l) | | 0.05 | 0.10 | 0.25 | 0.50 | 1.00 |
|---|---|---|---|---|---|---|
| surface | n=6 | 57 | 52 | 43 | 32 | 29 |
| tensions | n=8 | 34 | 29 | 21 | 15 | 14 |
| for | n=10 | 33 | 27 | 22.5 | 22 | 21.5 |

What we claim is:

1. Phosphoric esters of polyfluorinated alcohols consisting essentially of at least one isomer of phosphoric esters of polyfluorinated alcohols, said esters corresponding to the general formula:

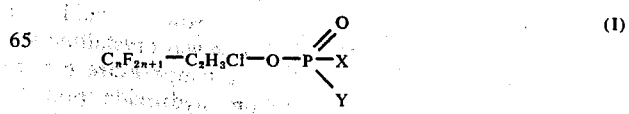

(I)

said two isomers corresponding to formulae (II) and (III):

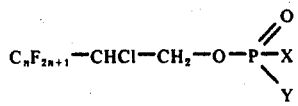  (II)

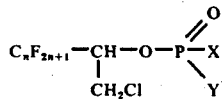  (III)

wherein $C_nF_{2n+1}$ is a perfluorinated aliphatic chain, $n$ is an integer from 2 to 18, X and Y are the same or different and are each a halogen atom; a hydroxyl radical; the group OM in which M is a metallic equivalent; an alkoxy, chloroalkoxy, hydroxypolyalkyleneoxy, or an aryloxy group; or the group —NZZ' in which Z and Z' are the same or different and are each a hydrogen atom or an alkyl, cycloalkyl, or aryl group.

2. Compounds of the formula

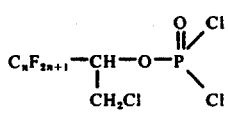

wherein $n$ is 2 to 18.

3. The compounds of claim 1 wherein X and Y are each a chlorine atom.

4. The compounds of claim 1 wherein X and Y are each a hydroxyl radical.

5. The alkali metal salts of the compounds of claim 4.

6. Process for the preparation of compounds of the formula

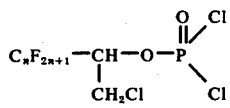

wherein $n$ is 2 to 18 which comprises reacting an olefin of the formula $C_nF_{2n+1}$—CH=CH$_2$ with phosphorous trichloride in the presence of oxygen or oxygen containing gases.

7. The process for preparing compounds according to claim 3 which comprises simultaneously reacting oxygen in the gaseous state, phosphorous trichloride and an olefin of the formula $C_nF_{2n+1}$—CH=CH$_2$ at a temperature of about —20° to 120° C under reduced atmospheric or elevated pressure.

8. The process of claim 7 wherein the reaction temperature is in the range from about 20° to 60° C.

9. The process of claim 7 wherein the molar ratio of phosphorous trichloride to olefin is between about 1 and 5.

* * * * *

UNITED STATES PATENT AND TRADEMARK OFFICE
CERTIFICATE OF CORRECTION

PATENT NO. : 4,034,022
DATED : July 5, 1977
INVENTOR(S) : Michel Demarcq and Joseph Sleziona It is certified that error appears in the above-identified patent and that said Letters Patent are hereby corrected as shown below:

Column 1, Line 11, reads "chain compounds", should read
--compounds--

Column 6, Line 15, reads "hydrolyzable Cl", should read
--hydrolyzable Cl%--

Column 6, Line 42, reads "hydrolyzable Cl", should read
--hydrolyzable Cl%--

Column 7, Line 3, reads "meeting", should read --melting--

Column 7, Line 4, reads "112°C", should read --122°C--

Column 8, Line 5, reads "molar per mole", should read
--mole per mole--

Column 8, Line 33, the word "basis" should be eliminated.

Column 8, Line 51, reads $-CH_2H_3Cl$ , should read $-C_2H_3Cl$

Signed and Sealed this

Fifteenth Day of November 1977

[SEAL]

Attest:

RUTH C. MASON
*Attesting Officer*

LUTRELLE F. PARKER
*Acting Commissioner of Patents and Trademarks*